(12) United States Patent
Heinzelmann et al.

(10) Patent No.: US 7,916,289 B2
(45) Date of Patent: Mar. 29, 2011

(54) APPARATUS FOR QUANTIFYING SHEAR STRESS ON A FORMULATION COMPRISING BIOMOLECULES

(75) Inventors: Udo Heinzelmann, Weissenhorn (DE);
Patrick Garidel, Norderstedt (DE);
Hans-Joachim Kern, Mittelbiberach (DE); Andreas Langer, Maselheim (DE); Juergen Weber, Ingerkingen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 330 days.

(21) Appl. No.: 12/057,424

(22) Filed: Mar. 28, 2008

(65) Prior Publication Data
US 2008/0246945 A1    Oct. 9, 2008

(30) Foreign Application Priority Data
Mar. 29, 2007    (DE) .................. 10 2007 015 136.7

(51) Int. Cl.
*G01N 21/01*    (2006.01)
(52) U.S. Cl. ........................................ 356/244
(58) Field of Classification Search ............ 356/32–38, 356/244–246
See application file for complete search history.

(56) References Cited

U.S. PATENT DOCUMENTS

| | | | |
|---|---|---|---|
| 4,587,837 A | | 5/1986 | Newbould |
| 4,752,131 A | * | 6/1988 | Eisenlauer et al. ........... 356/338 |
| 5,522,274 A | | 6/1996 | Behar et al. |
| 5,798,827 A | * | 8/1998 | Frank et al. .................. 356/39 |
| 5,900,539 A | | 5/1999 | Tremblay et al. |
| 6,494,084 B1 | | 12/2002 | Roberts et al. |
| 6,779,382 B2 | | 8/2004 | Rupieper et al. |
| 7,242,474 B2 | * | 7/2007 | Cox et al. ..................... 356/338 |
| 7,312,088 B2 | * | 12/2007 | Farquharson ................ 436/169 |

FOREIGN PATENT DOCUMENTS
GB    2120793    12/1983
* cited by examiner

*Primary Examiner* — Michael P Stafira
(74) *Attorney, Agent, or Firm* — Michael P. Morris; Wendy Ann Petka; Edward S. Lazer

(57) ABSTRACT

The present invention relates to an apparatus for determining the shear sensitivity of particles in solutions and methods of determining the respective shear velocities or the respective shear stress.

13 Claims, 5 Drawing Sheets

APPARATUS FOR QUANTIFYING SHEAR STRESS ON A FORMULATION COMPRISING BIOMOLECULES

BACKGROUND TO THE INVENTION

1. Technical Field

The invention relates to an apparatus for simulating the shear stress which is exerted on particles dispersed in solution, such as, for example, proteins. The invention further relates to a method of determining the shear stress in the components needed for filling (filters, filling needles, pumps, hoses, etc), particularly for filling a liquid that contains dispersed particles (such as biomolecules/proteins/macromolecules). The present invention further comprises the use of a shear stress application (PSA) for simulating shear stress in processing and filling plants for solutions with high molecular components (such as proteins, DNA, antibodies, etc.).

2. Background

In aseptic manufacture, liquid products are generally transferred into so-called primary packaging systems.

On its way from the manufactured product to the primary packaging, the product, which may in some cases be delicate or fragile, passes through numerous industrial processes associated with filling, such as stirring, sterile filtration, pumping, transporting, filling, etc. processes or devices. Each of these processes necessarily includes fluid flows in which shear velocities are produced. These shear velocities represent a mechanical shear stress for the particles dispersed in the solution (e.g. proteins) and may lead to damage or even to the destruction of the product that is to be filled, depending on the strength and stability of the product.

The problem was therefore to provide a process that allows a systematic, reproducible collection of data on the correlation between shear stress and stability of the particles dispersed in the solution.

In order to determine the effects of the various filling processes or of the process as a whole on the stability and quality of the product, a shear stress application was developed and used (e.g. for process control). In addition, it is possible using the application in order to determine product sensitivity in the aqueous system, and thereby assess suitable formulations and facilitate the discovery of suitable formulations.

SUMMARY OF THE INVENTION

The apparatus described constitutes the technical means for solving the problem.

The present invention relates to an apparatus consisting of at least the following parts:
a) mechanical enclosure,
b) two complementary cylindrical bodies (e.g. syringes) made entirely of glass
c) connected via a defined cannula to Luer-Lok connections,
d) two (syringe) plungers, fitting into the glass bodies in b),
e) locking holders,
f) optionally locking abutments,
g) drive,
h) digital control unit,
the glass bodies and the cannula being connected to the mechanical enclosure (the system).

The present invention develops and implements the idea of a process for adjusting the defined shear velocity and duration of stress for solutions with high-molecular ingredients (proteins, DNA, antibodies, etc.) of the type that occur on a large industrial scale in processing and bottling plants.

The adherence to criteria such as a low sample size and optimum process compatibility (use of identical materials) are made possible by the use of two complementary syringes joined together by a defined cannula. The effects of stress on proteins, for example, are quantified analytically, e.g., by PCS or turbidity measurements.

The invention relates to the development and use of the shear-stress application (PSA) apparatus for quantifying the effects of different formulations on the protein stability with freely selectable parameters such as shear velocity and the duration of the stress on the protein (example: antibody IgG1).

The intensity of the shear stress and the duration of the stress bring about a change in the particle size (e.g., protein aggregation or division). The degree of protein aggregation ("protein degradation") increases with the intensity of the stress. This effect is reproducible by the PSA, and thus, for example, allows the protein stabilities of different formulations to be compared. The effects of the shear stress on the macromolecules (e.g. protein aggregation) are quantified analytically, e.g. by PCS or turbidity measurements.

The invention also relates to the development and use of shear stress application (PSA) for determining the characteristics of molecular stability (e.g. protein aggregation) by defined shear velocities and duration of stress. Stress curves indicate how much the protein quality is dependent on the shear stress or shear duration. The data obtained are used to make pronouncements as to the sensitivity of the proteins. The effects of stress on the molecules (e.g. protein aggregation) are quantified analytically, e.g. by PCS or turbidity measurements.

The invention also includes the development and use of a shear stress application (PSA) for tests on filters to determine their effect on protein quality caused by shear stress at defined volumetric flows. The effects of shear stress on the molecules (e.g. protein aggregation) are quantified analytically, e.g., by PCS or turbidity measurements.

The invention further relates to the development and use of a shear stress application (PSA) for comparing the foaming tendency of different protein solutions.

A PSA syringe partly filled with air causes the aqueous protein solution to mix with the air and form a foam during application. The intensity of foaming is dependent on the shear velocity and thus enables different solutions to be compared quantitatively.

It is possible, if desired, to equip the PSA with an integrated optical measuring system in order to be able to carry out measurements of turbidity and concentration online. The mode of operation of the present invention is as follows:

Two entirely glass syringes (2-20 ml capacity), after being filled with the solution to be tested, are joined together by a low-air connection using a specially prepared cannula with Luer-Lok connections. The syringes are then installed in the apparatus (PSA), the syringe bodies and cannula being connected to the system. Two locking holders provided on the finger rests of the syringe plungers ensure a fixed positioning of the plungers and hence the respective emptying and filling of the syringe bodies through the cannula as the syringe bodies are moved up and down by electromechanical drive means. Specially developed software makes it possible to adjust the parameters of the stroke speed, and the number of repetitions and thus ensures defined procedures. The selection of a defined shear stress is carried out by means of the dependency of the shear stress on the cannula diameter and speed in the flow of aqueous fluid.

Shear rates of from 0 to about 200,000 l/s (laminar/turbulent) and a shear duration that can be selected within a wide range can be set in the PSA, the shear duration corresponding to an assumed cannula length. The molecular particles are mechanically loaded by the different flow velocities of the medium in the cannula depending on the shear velocity selected. The faster a fluid flows through a cannula, the greater the shear stress on the molecular particles or on particles dispersed in solution.

The purpose and effect of the PSA apparatus is to subject molecules (e.g. proteins) in solution to a mechanical load such that the aggregation of the molecules (change in conformity) as a result of the shear stress changes measurably, to enable the stability characteristics of the molecules under mechanical stress to be determined by analytical processes such as e.g. PCS or turbidity measurements.

The particular advantage of the glass bodies used (e.g. glass syringes) is that they do not need any additional materials. The bodies/syringes are also "leaktight" without any such additional materials and have very low coefficients of adhesion and friction as a result of the liquid wetting the plunger and cylindrical body. Moreover, many medical products are transported and stored in glass containers. Therefore, the use of glass bodies in the apparatus according to the invention is particularly convenient for production and hence advantageous. Plastic syringes usually have rubber seals. The rubber is normally also siliconised to minimise the frictional forces. The interactions between proteins and synthetic substances or silicon lubricants are not fully known and may involve some risks. "Extractables" and "leachables" in particular are currently being discussed as undesirable components. In addition, the PSA may operate by a reciprocating movement, whereas plastic bodies (syringes) are not designed for such operations. When plastic bodies are used, the coating may come off or silicon oil may go into solution. Accordingly, the present invention requires the use of bodies made entirely of glass.

It is also advantageous or essential to the invention that the up and down movement should be performed using the movement of the cylindrical glass bodies.

The particular advantages are also in the
a) absolute affinity of the process with processing and bottling plants (use of identical materials)
b) use of small volumes of sample (1-20 ml)
c) carrying out of stability studies regarding shear stress and duration
d) versatility of use, e.g. for
　stability tests on macromolecules
　production of defined amounts of foam
　filter tests
　discovering formulations
　determining the shear gradients present in filling or bottling plants
　simulation of filling or bottling plants Particular applications that may be envisaged for the present invention include
　the process safety control of liquid products (parenteral preparations)
　the discovery of formulations The invention does not arise from the prior art. The following conventional methods and apparatus are known:

The document "The Effect of Membrane Filtration Upon Protein Conformation" (George A. Truskey et. al.) describes the effects of shear velocity in membrane pores on protein conformation.

The document "Do Protein Molecules Unfold in a Simply Shear Flow" (Juan Japse et. al.) describes the effects of shear velocity in a capillary on protein conformation using fluorescence spectroscopy.

The document "Effect of High Shear on Proteins" (Yuh-Fun Maa et. al.) describes the effects of shear gradients on protein aggregation.

The document "Shear effects on enzymes" (Stanley E. Charm et. al.) describes the effects of shear velocity on enzyme conformation.

The state of the art is to produce a fluid with shear velocity in different ways. This is often done using rotary bodies in which the fluid is accelerated, or using capillaries through which the solution to be measured is forced by a pump or by pressure. The disadvantages of these procedures are obvious. Rotationally driven fluids have a tendency to sediment, i.e., the particles dispersed in the solution form local concentrations and/or deposits. There is also a possibility that solubility limits will be reached and as a result proteins will be precipitated. In addition concentration alters the viscosity characteristics of the liquid and thus leads to non-determinable measured variables. The techniques involving the use of a capillary lead to batch-type operation when pumps or pressure are used (usually nitrogen) and therefore do not allow the shear duration to be varied freely. Also, the use of a pump is questionable, as the pump itself exerts shear stress on the test solution.

BRIEF DESCRIPTION OF THE DRAWINGS

Please be advice that the following terms used in the drawings have the following meanings:
　FIGS. 2 & 3: Trübung means turbidity
　Nr. means No.
　Zyklen means Cycles
　FIG. 4: Trübung means turbidity
　Nr. means No.
　Scherrate means Shear rate
　FIG. 5: Trübung means turbidity
　Zyklen means Cycles
　Messung means Measurement

DETAILED DESCRIPTION OF THE INVENTION

Figure 1A:
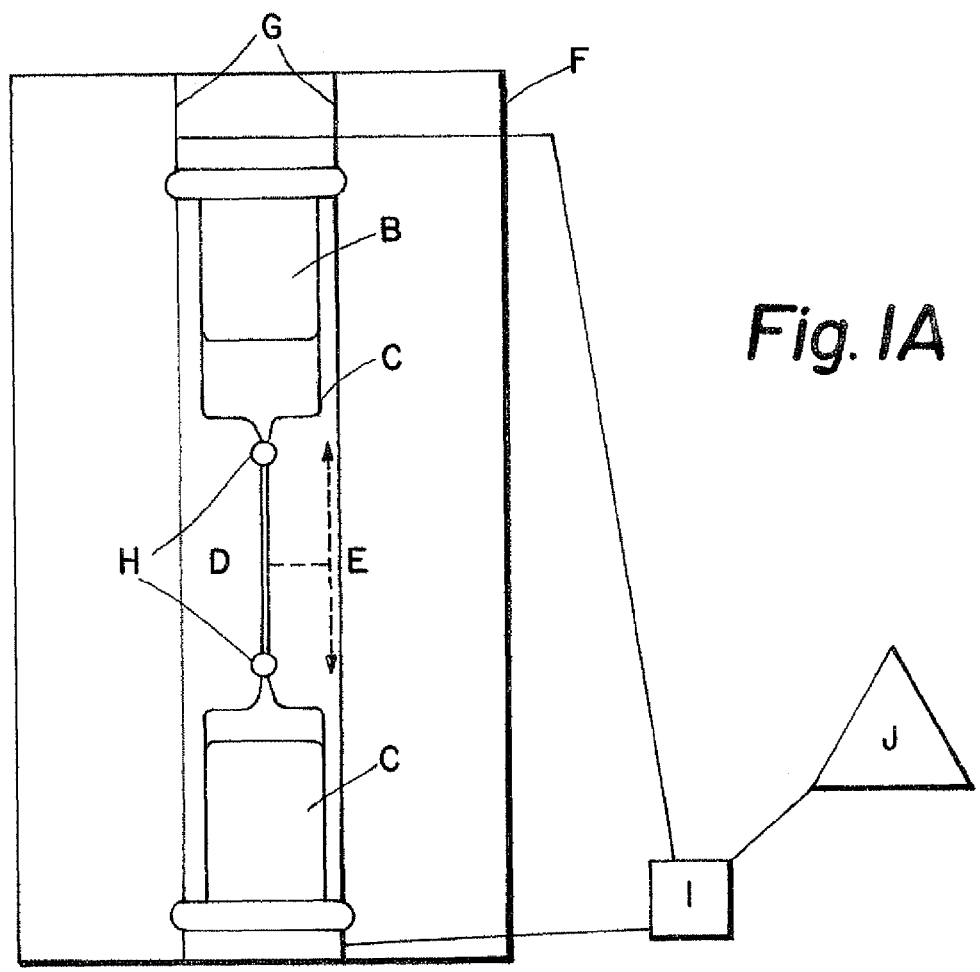
FIG. 1A is a schematic diagram of an apparatus of the present invention with the following components labelled:
A: locking stop
B: plunger (e.g. syringe plunger)
C: cylindrical glass body (e.g. syringes made entirely of glass)
D: cannula/cannula tube
E: travel distance of the cannula tube and syringe cylinder: up/down
F: mechanical enclosure
G: locking holder
H: Luer-Lok connections
I: drive
J: digital control unit

The shear stress application is carried out for two main purposes:

On the one hand, to simulate stress on proteins of the type that prevails in the process of decanting aqueous protein solutions into filling needles. The main requirements are a high affinity for the process, a low sample requirement, the use of materials that are inert in the presence of proteins (glass, stainless steel) and user independence.

On the other hand, to produce a defined shear stress for evaluating and comparing protein stabilities for developing the formulation of aqueous protein solutions. The chief objective is to create reproducible conditions for denaturing proteins.

The mechanical stressing of the particles in aqueous solution is based on flow effects that occur in any tubular flow. The flow velocity of the medium is equal to zero on the wall surface, while the maximum velocity occurs in the middle. The velocity profile of a laminar flow in a tube (cannula) is parabolic. If the parabolic mathematical function is derived from the flow, this results on average in the shear velocity $\gamma$ (gamma point) of the flow. The shear velocity is proportional to the volumetric flow and in inverse proportion to the power of three of the characteristic tube diameter. The application makes use of this connection, from the knowledge of the cannula diameter used and the constantly adjustable volumetric flow.

The apparatus consists essentially of three basic components:
- in-built receiving socket for the complementary syringes with a Luer-Lok connection for syringe sizes from 2 ml to 20 ml and a freestanding housing with an operator safety device,
- electromechanical drive (stepping motor) for the lifting pin for actuating the syringe cylinders,
- digital stepping motor control unit and PC software The protein shear stress application primarily comprises a process that enables the particles dispersed in an aqueous solution to be stressed in a mechanically reproducible manner in a cannula using the volumetric flow-dependent shear velocity. Thanks to the provision of two wholly glass syringes operating in complementary fashion in which the liquid to be tested is changed over once per operating cycle, it is theoretically possible to stress the test solution for an unlimited length of time without using any additional sample material. The process requires no more than 1.5 ml of sample material. In order to keep the shear velocity with the physically coupled shear stress constant irrespective of viscosity depending on the parameterisation, the stroke movement is controlled not by the force acting thereon but by the volumetric flow that is a product of the stroke speed.

The application has a high process affinity in two respects: (1) on the one hand because it uses only two pharmaceutically and medically safe materials, such as glass and stainless steel; and (2) on the other hand because it uses original filling needles of the kind used in filling processes.

The cannulas used in the application (original filling needles with different diameters) each have a Luer-Lok connection at their ends, that is welded on specially by a LASER welding process, to form a fluidtight seal. This welding process makes it possible to produce a funnel-shaped inlet that eventually transfers the test solution from the syringe into the cannula, as far as possible with no turbulence. The Luer-Lok connection makes it possible to accommodate syringes with a corresponding mating connection and is thus compatible with various syringe sizes. The filling of the syringes takes place independently of the application and can conveniently be done on the laboratory bench. With the aid of a locking device (e.g. a stand) for a syringe, if necessary the syringes can be coupled to one another in airfree manner using the cannula tube.

The effect of the PSA is to apply mechanical stress in reproducible manner and over a wide range to particles dispersed in solution (e.g. macromolecules/proteins) by the shear stress application. The aim here is to simulate, inter alia, shear velocities of the kind that occur in filling processes (pumps, hoses, filters, filling needles etc.) in order to test the processability of the product using a reduced volume (process safety). In addition, the quality of the formulation can also be tested using the protein stability (discovery of formulation).

The particular advantage of using the shear stress application is the possibility of simulating the entire range of stresses occurring during filling, in a manner that is compatible with the process, using the smallest volume of sample, and also to be able to make useful pronouncements as to the protein stability for finding a suitable formulation.

Terms and designations used within the scope of this description have the following definitions specified below. The general terms "containing" or "contain" also encompass the more specific term "consisting of". Moreover, singulars and plurals are not used in a restrictive capacity.

The terms "device", "PSA", "apparatus", "shear stress apparatus", "shear stress application" are all equivalent. "PSA" stands for "Protein Shear stress Application".

The term "dispersed particles" denotes particles that are homogeneously distributed in a fluid phase, preferably in an aqueous solution, their size preferably being in the nanometre range. These particles may be for example proteins, deoxyribonucleic acid (DNA) or other macromolecules.

The dispersed phase can generally be divided up as follows, according to particle size:
- dissolved in a molecular dispersion relates to particle sizes<1 nm such as e.g. in true solutions/in fluid phases,
- dissolved in a colloidal dispersion relates to particle sizes from 1 nm to 1 µm, e.g. in protein solutions,
- dissolved in a coarse dispersion relates to particle sizes>1 µm, e.g. as in globules of milk fat.

If the particles dispersed in a solution are all the same size, this is referred to as a monodispersed system. Within the scope of the systems used in the present invention, a monodispersed mixture of particles (e.g. proteins, DNA, etc.) is present at the start of the experiment, in the most favourable case. Proteins may reach a size of up to about 3600 kDa. A class G antibody generally has a size of about 11 nm hydrodynamic diameter. Depending on the conformation a DNA strand may be more than 1 µm long. The size is therefore geometrically relative.

The shear stress simulation promotes aggregate formation as a result of the change in conformation, and then as a rule the system can be referred to as a colloidally dispersed system of a polydispersed type.

The term "filling" denotes a total process comprising all the subsidiary steps from the delivery of a product to the packaged unit. These include, for example, in the filling of pharmaceutical fluids, the subsidiary steps of filtration and filling of the vials using filling needles.

The term "shear stress" refers to the mechanical stress on the particles dispersed in the solution caused by the fluidic velocity gradient of a flow in a pipeline.

The "defined cannula" consists of three parts. A cannula tube suitable for medical use which is 120 mm long, and two standardised Luer-Lok connections (female) which are welded to the ends of the cannula by LASER welding. The 6% cone (Luer) in conjunction with the welding technique used forms a fluidically favourable transition from the Luer to the internal diameter of the cannula tube. Preferably, three different internal diameters (ID) are used: ID=0.6 mm, 1 mm and 2 mm. The system is therefore suitable for coupling two syringes with Luer-Lok connections (male).

"Luer-Lok" is a standardised connecting system for cannulas, syringes and infusion tubes in the medical field.

The seal is achieved by means of a conical construction of the connecting elements, the so-called Luer cone. The inner cone on one side of the connection is referred to as "female", while the outer cone on the other side is "male". If the cone is expanded to include a thread with a lock nut for securing or locking the connection against accidental release the system is referred to as Luer-Lok. The connection opens and closes with a half-turn. The Luer-Lok system ensures compatibility between different manufacturers and is internationally recognised. The design is described in the DIN EN standard 1707: 1996 "Cone connections with a 6% (Luer) cone for syringes, cannulas and certain other medical equipment—Lockable cone connections" and in DIN EN standard 20594-1:1993 "Cone connections with a 6% (Luer) cone for syringes, cannulas and certain other medical equipment". The term "Luer" dates back to the German instrument maker Hermann Wülfing Luer who worked in Paris.

"Vial" refers to an injection bottle or pierceable bottle.

By "foaming" is meant the tendency of a liquid to foam by the inclusion of gas.

The term "stability", particularly "protein stability" refers to the resistance of the protein for remaining unaffected in its functionality or conformity against external influences such as e.g. ionic strength or the mechanical effects of force.

"Proteins" are macromolecules and belong to the basic components of all cells. Human proteins may be up to 3600 kDa in size.

"PCS" stands for Photon Correlation Spectroscopy and makes it possible to determine the hydrodynamic size of particles dispersed in an aqueous solution. The measuring range is from 1 nm to several μm.

The "turbidity measurement" is a process that measures the scattered light intensity—caused by particles dispersed in solution—of a light beam passing through the solution. A change in the perceptible scattered light intensity is directly proportional to the change in the particle size and the number of particles in the solution.

The term "complementary cylindrical wholly glass body" denotes bodies in the sense of containers that are conically shaped in the region of the outlet. There should not be any sharp edges (particularly with regard to flow). The preferred example of such a body is a syringe. The particularly preferred syringe model is the FORTUNA® OPTIMA® wholly glass syringe (in sizes: 2, 5, 10 and 20 ml) manufactured by Poulten & Graf GmbH, Am Bildacker 3-7, 97877 Wertheim.

The term "complementary" or "complementary syringes" refers to the fact that the two bodies or syringe complement each other in use, specifically by acting alternately as the receiving container and removing container.

The "shear velocity" is an average of the measurements of the geometric ratio of length to width of a volume element of the laminar flow of liquid, as described. The unit is $s^{-1}$ and is thus a measurement of velocity. The absolute value is proportional to the shear load.

The "shear load" is identical to the "shear stress".

EXAMPLES

The data that follow are generated by forcing a protein solution, for example, through a cannula with a notional length of 12 m (corresponding to 100 cycles) at different shear velocities (protein stress level) and then measuring the turbidity of the stressed protein solution (nephelometry, unit FNU).

In the following tests, shear rates of from 0 to 64,000 l/s and different numbers of cycles are simulated. The variation in the number of cycles corresponds to a particular length of cannula. 1 cycle denotes a cannula 12 cm long, 100 cycles denote 12 m of cannula length. In addition, an investigation is carried out as to whether the inclusion of air when filling the syringes has significant effects (interface effects) on the proteins, with the result that no significant differences can be detected.

Example 1

The apparatus consisting of two wholly glass syringes, a cannula tube and a mechanical construction for moving the syringes (cf. FIG. 1) is used for two different protein formulations to demonstrate the dependency of the protein aggregation/degradation on the duration of shear stress acting on the proteins. Specially developed software (software code: {81566AFO-A9CD-4EFD-A1E1-F07AF6DD2507}) enables the parameters of stroke speed and number of repetitions to be set and thus allows defined procedures to be carried out.

Figure 2:
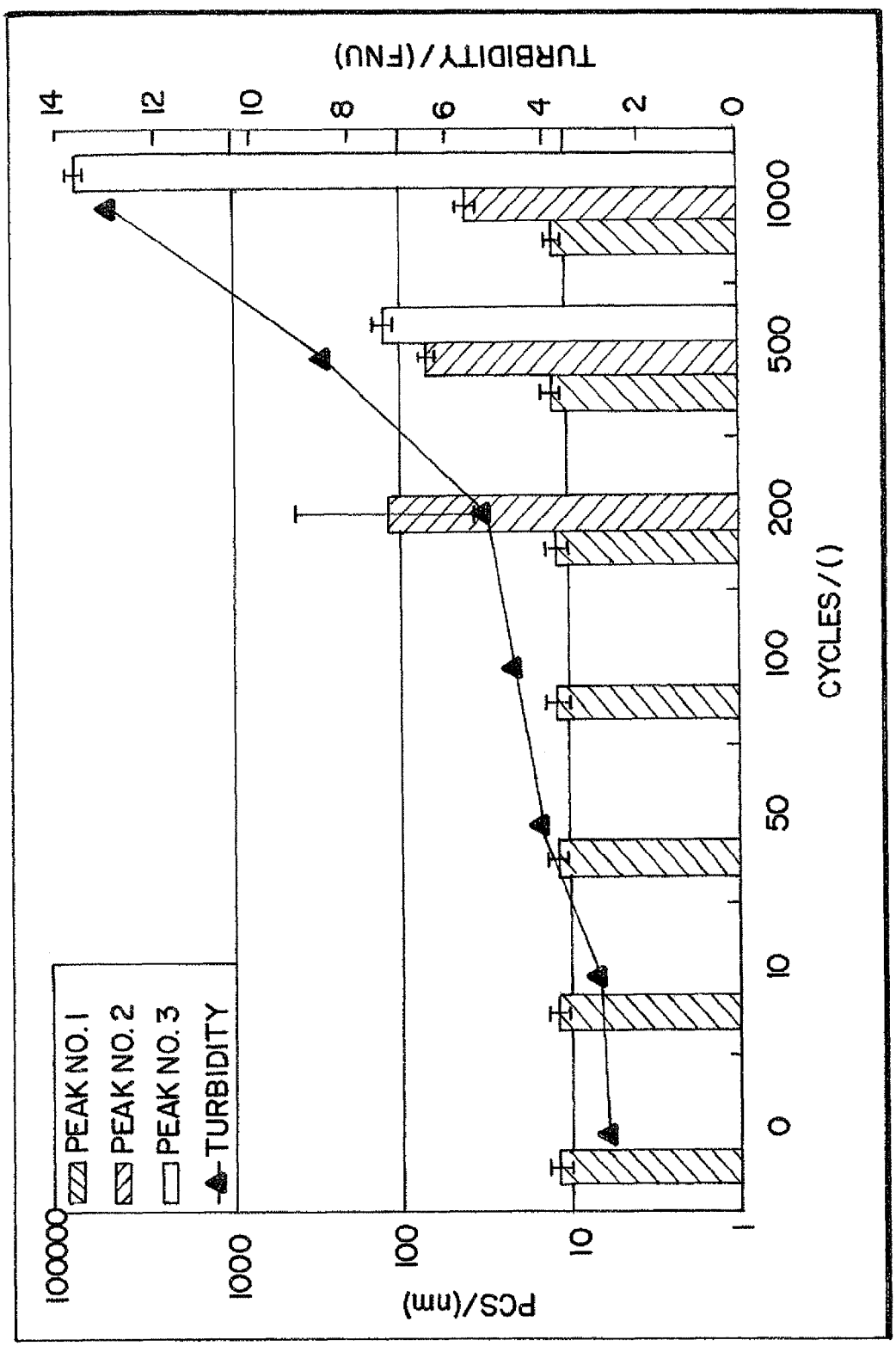
FIG. 2 is a graph showing the effect of the variation in the shear duration (number of cycles) at a constant shear rate of 4800 l/s.
Figure 3:
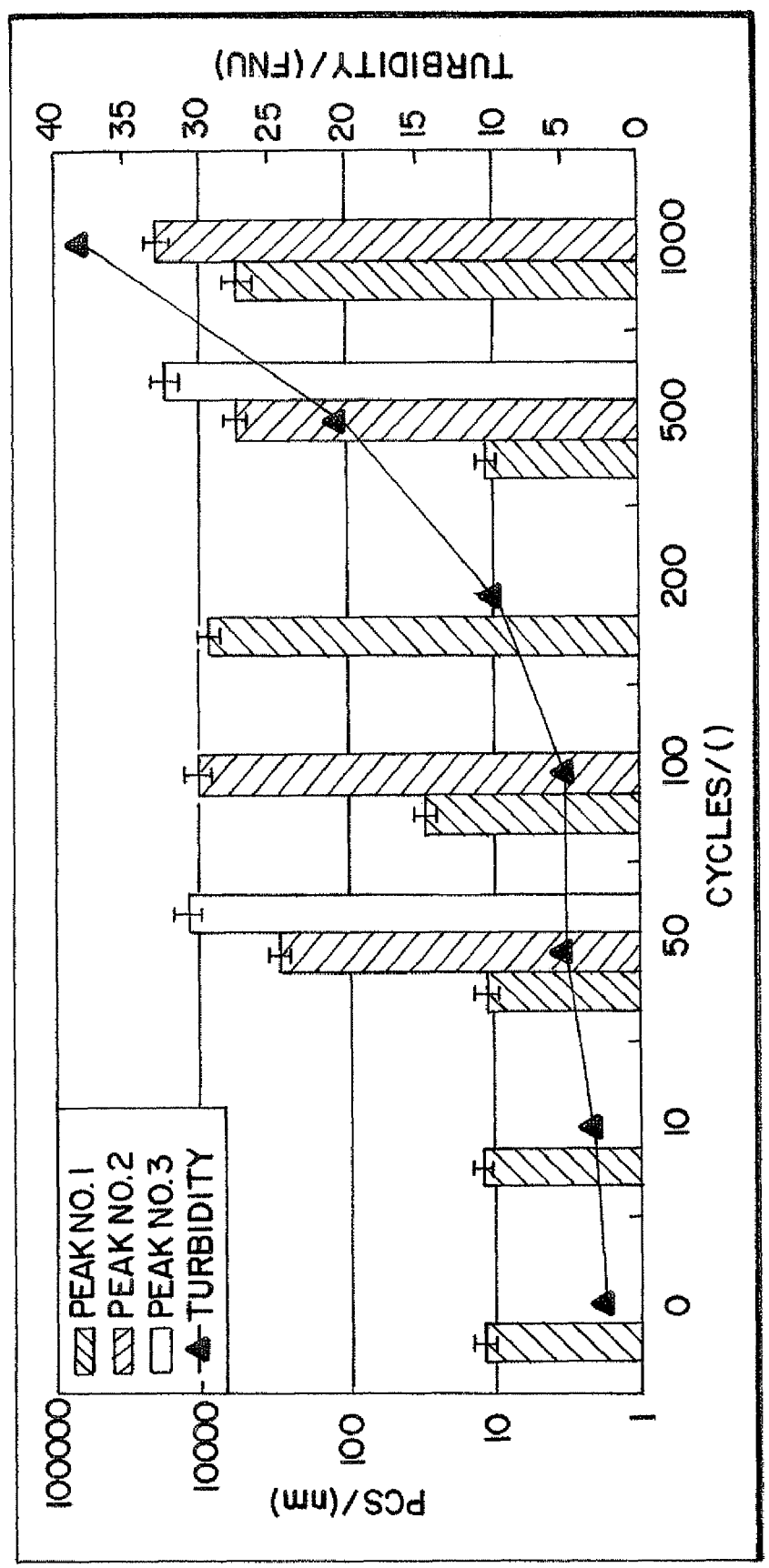
FIG. 3: is a graph showing the effect of the variation in the shear duration (number of cycles) at a constant shear rate of 64000 l/s.

FIGS. 2 and 3 contain the results of the two formulations at a constant shear velocity and over different shear times (number of cycles). The curves show that as the shear stress increases, aggregated particles (PCS measurement) are formed and the opalescence (turbidity) of the solution increases considerably. The original particle size at the start of the measurement is about 11 nm in diameter.

Example 2

The apparatus consisting of two wholly glass syringes, a cannula tube and a mechanical construction for the movement of the syringes (FIG. 1) is used for a protein formulation in order to demonstrate the dependency of the protein aggregation/degradation on the intensity of shear stress acting on the proteins. Specially developed software (software code: {81566AFO-A9CD-4EFD-A1E1-F07AF6DD2507}) enables the parameters of stroke speed and number of repetitions to be set and thus allows defined procedures to be carried out.

Figure 4:
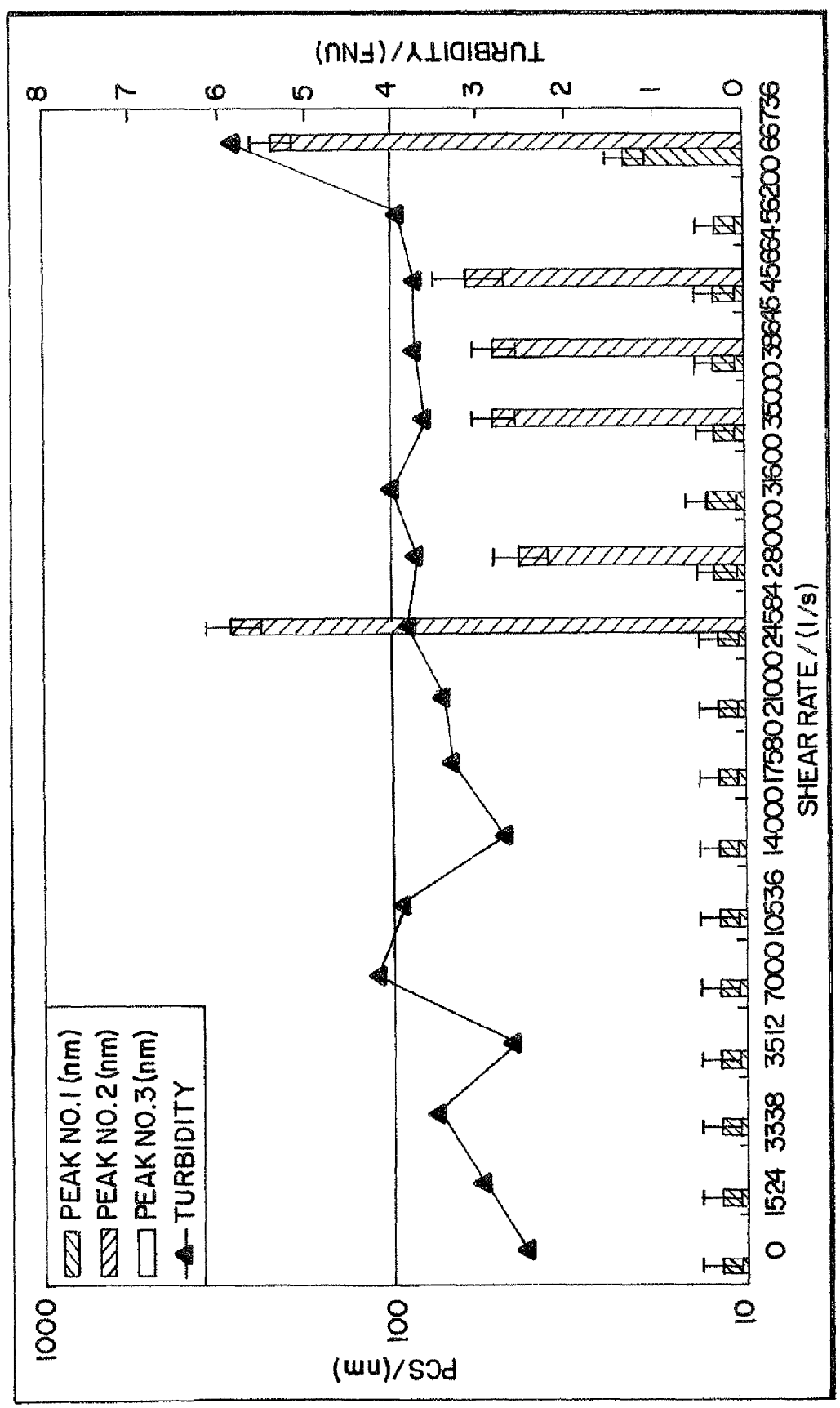
FIG. 4: is a graph showing the effect of the variation in the shear rate at a constant cycle number of 100 (turbidity and particle size as the shear rate increases).
Figure 5:
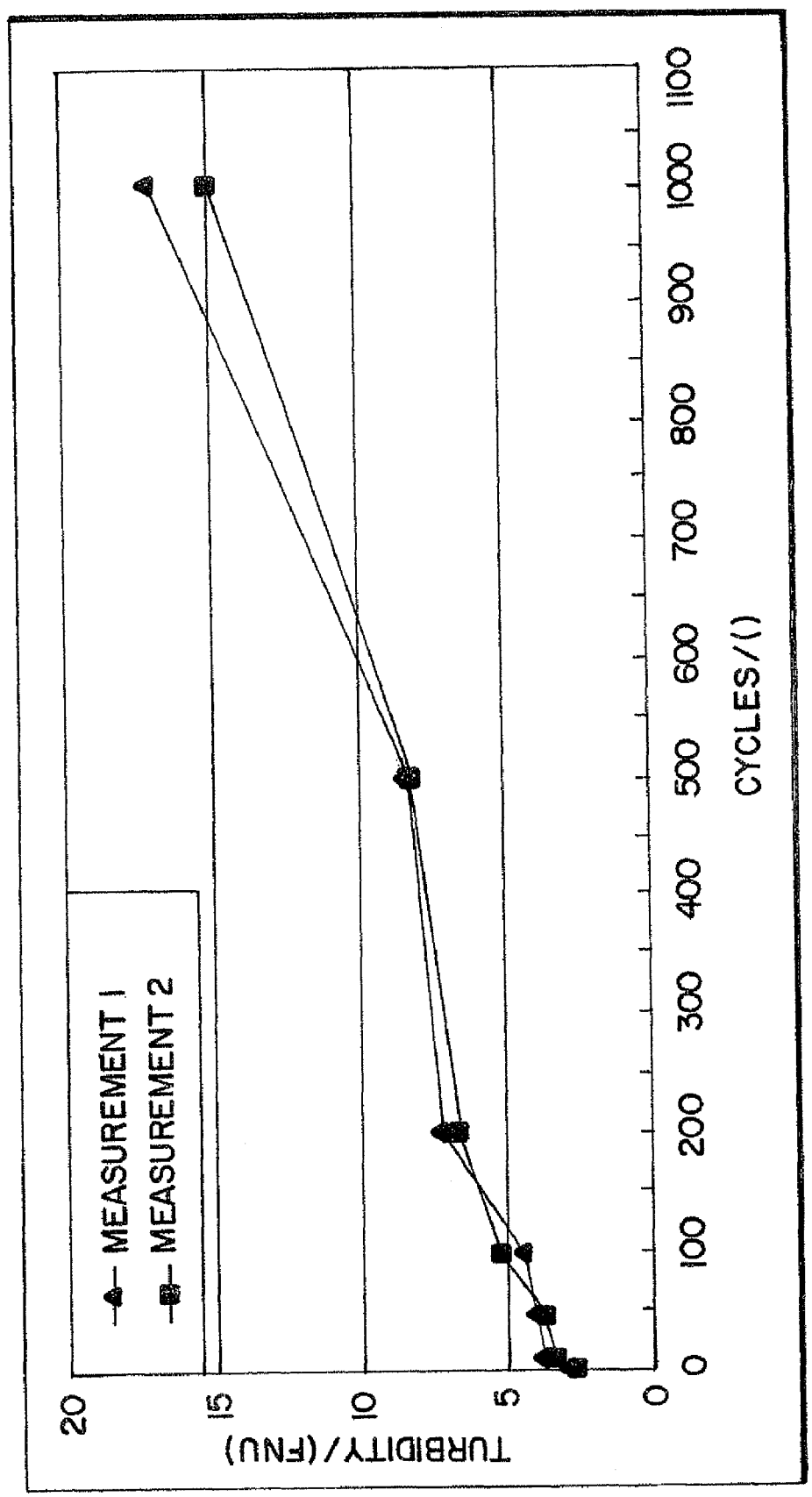
FIG. 5: is a graph showing repeat measurement of turbidity on day 2 with constant shear rate parameters (28000 l/s) (reproducibility).

FIG. 4 shows that a threshold value of the shear stress intensity (shear rate) has to be exceeded for a change to occur in the protein size. This threshold value is about 30 000 l/s in this experiment. If this threshold value is then set as the minimum value for a further experiment, the functionality of the protein shear stress application can be demonstrated by the reproducibility of the measurements obtained. FIG. 5 shows that with a fixed shear velocity (above the threshold value) the turbidity of a protein solution increases equally strongly with a constant increase in the shear duration for two independent measurements. The measurements obtained are thus reproducible.

Example 3

Figure 1B:
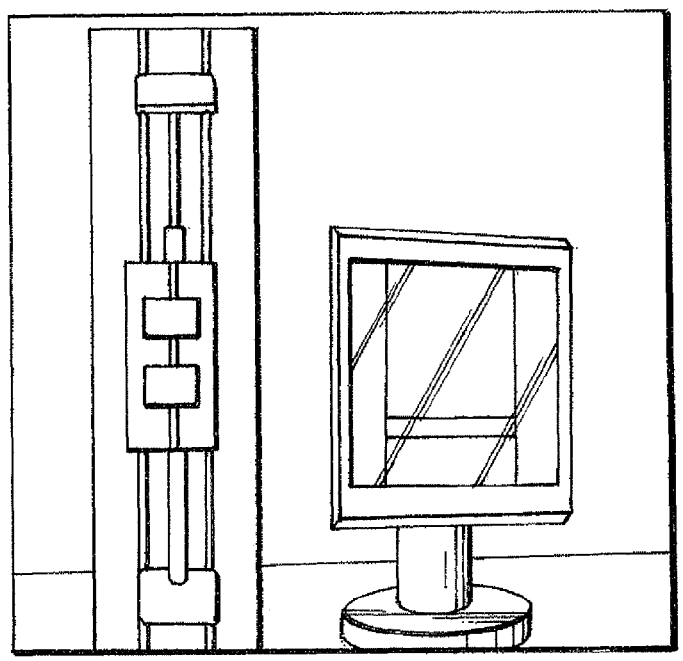
FIG. 1B is a photo of the PSA.

Correlation tests are carried out on the simulation of protein shear stress using protein shear stress application (PSA, according to FIG. 1).

On the one hand, the effects of the process components of silicon tubing, sterile filter, tube pump, rotary flask filler, filler needle and impact effects of the kind that occur when filling containers, for example, are investigated. This is carried out separately for two different, protein-containing liquid products by turbidity-photometric and photon-correlation-spectroscopic measurements and measurement of the molecular size of the particles in the liquid by the SDS-Page method of analysis.

In addition, two different proteins with different formulations are stressed to different levels using shear stress application. Curve/measurement data are recorded (identical analyses to those in the process tests described in Examples 1 and 2), resulting from shear rates of 100 to about 160,000 l/s and a cycle width of from 1 to about 100. The results from the tests on process and application are plotted against one another and correlated, to establish the parameterisation for the shear stress application, on the one hand, and to quantify the shear stress on the other hand (characteristic of the shear velocity yields the mathematical model of the shear stress application), occurring in the respective process component.

In addition, pH tests are carried out to determine the shear stress sensitivity of antibodies.

What is claimed is:

1. An apparatus for determining shear stress load on particles in a liquid comprising
   a mechanical container connected to
   two complementary cylindrical bodies made entirely of glass, each cylindrical body having a first open end, each open end having a plunger fitted therein,
   a cannula that connects the two cylindrical bodies with Luer Lok connections at respective second ends of the cylindrical bodies,
   the mechanical container comprising a first
   locking holder for engaging an end of a plunger extending out of one of the cylindrical bodies and a second locking holder for engaging an end of a plunger extending out of the other of the cylindrical bodies and optionally a locking abutment, oriented adjacent to at least one of the locking holders,
   a drive apparatus operably connected to the mechanical container and either a cylindrical body or a plunger to move the cylindrical bodies or plungers in a reciprocating fashion with respect to the other, and
   a digital control unit operably connected to the mechanical container for controlling operational parameters.

2. The apparatus according to claim 1, wherein the apparatus additionally contains an integrated optical measuring system.

3. The apparatus according to claim 1, wherein the glass bodies can hold about 2 ml to about 20 ml in capacity.

4. The apparatus according to claim 1, wherein the glass bodies are syringes.

5. The apparatus according to claim 1, wherein the drive is an electromechanical stepping motor for moving the glass bodies up and down.

6. The apparatus according to claim 1 characterised in that software is installed for controlling the parameters of stroke speed and the number of repetitions.

7. The apparatus according to claim 1, wherein the internal diameter of the cannula is selected from about 2 mm, about 1 mm or about 0.6 mm.

8. A method for determining the shear stress load of a particle dispersed in solution, during the filling of the solution, in an apparatus comprising a mechanical container connected to two complementary cylindrical bodies made entirely of glass, each cylindrical body having a first open end, each open end having a plunger fitted therein,
   a cannula that connects the two cylindrical bodies with Luer Lok connections at respective second ends of the cylindrical bodies,
   the mechanical container comprising a first locking holder for engaging an end of a plunger extending out of one of the cylindrical bodies and a second locking holder for engaging an end of a plunger extending out of the other of the cylindrical bodies and optionally a locking abutment oriented adjacent to at least one of the locking holders,
   a drive apparatus operably connected to the mechanical container and either a cylindrical body or a plunger to move the cylindrical bodies or plungers in a reciprocating fashion with respect to the other, and
   a digital control unit operably connected to the mechanical container for controlling operational parameters, the method comprising the following steps:
   a) filling one or both cylindrical glass bodies with said solution,
   b) moving the plungers from step a) repeatedly up and down over the cannula in the apparatus, and
   c) measuring the particle aggregation/particle destruction.

9. The method according to claim 8, wherein an analytical quantification of the particle aggregation/particle destruction is carried out by Photon Correlation Spectroscopy (PCS) or turbidity measurements.

10. The method according to claim 8, wherein the particle dispersed in solution is a high-molecular component such as biomolecule.

11. The method according to claim 10, wherein the high-molecular component is a biomolecule selected from the group consisting of proteins, deoxyribonucleic acid (DNA) and ribonucleic acid (RNA).

12. The method according to claim 11, wherein the biomolecule is a protein which is an antibody.

13. The method according to claim 8, wherein the filling is carried out in the absence of air.

* * * * *